United States Patent [19]

Mendershausen et al.

[11] Patent Number: 5,344,571

[45] Date of Patent: Sep. 6, 1994

[54] METHOD FOR SEPARATING ISOANALYTES AND MEASURING ANALYTES IN FLUIDS

[75] Inventors: Philip B. Mendershausen; Vitauts Jurevics, both of Dallas, Tex.

[73] Assignee: University of Texas System Board of Regents, Dallas, Tex.

[21] Appl. No.: 837,208

[22] Filed: Feb. 18, 1992

[51] Int. Cl.$^5$ ................... B01D 61/00; B01D 21/01
[52] U.S. Cl. ................... 210/723; 210/767
[58] Field of Search ............... 210/645, 646, 651, 653, 210/654, 655, 675, 723, 726, 729, 730, 731, 767, 199, 295, 321.6, 321.63, 321.69, 321.7, 321.72, 321.75, 321.84, 416.1, 428, 433.1, 443, 85; 422/50, 55, 68.1, 101, 102, 104; 436/13, 71, 16, 177, 175, 178; 530/412, 414, 419

[56] References Cited

U.S. PATENT DOCUMENTS

| | | | |
|---|---|---|---|
| 3,425,560 | 2/1969 | Smythe | 210/321.6 |
| 3,572,994 | 3/1971 | Hochstrasser | 210/321.6 |
| 3,963,613 | 6/1976 | Chibata et al. | 210/321.6 |
| 4,039,285 | 8/1977 | Teipel | 252/408.1 |
| 4,096,136 | 6/1978 | Ayers et al. | 424/101 |
| 4,147,606 | 4/1979 | Golias | 204/180 S |
| 4,167,467 | 9/1979 | Golias | 204/180 S |
| 4,188,188 | 2/1980 | Willner et al. | 252/408.1 |
| 4,210,557 | 7/1980 | Handschuh | 210/723 |
| 4,215,993 | 8/1980 | Sanders | 252/408.1 |
| 4,226,713 | 10/1980 | Goldberg | 210/716 |
| 4,234,317 | 11/1980 | Lucas et al. | 210/738 |
| 4,309,188 | 1/1982 | Bentzen . | |
| 4,366,244 | 12/1982 | Pascal | 252/408.1 |
| 4,399,030 | 8/1983 | Hlavinka et al. | 210/321.69 |
| 4,399,217 | 8/1983 | Holmquist et al. | 435/28 |
| 4,414,326 | 11/1983 | Goldberg | 435/28 |
| 4,444,597 | 4/1984 | Gortz et al. | 210/646 |
| 4,851,335 | 7/1989 | Kerscher et al. | 435/28 |
| 4,892,815 | 1/1990 | Kerscher et al. | 435/28 |
| 4,923,439 | 5/1990 | Seidel et al. | 436/71 |
| 4,968,422 | 11/1990 | Runge et al. | 210/321.72 |
| 4,968,432 | 11/1990 | Antwiler | 210/677 |
| 5,004,548 | 4/1991 | Richalley et al. | 210/646 |
| 5,057,226 | 10/1991 | Antwiler | 210/641 |
| 5,118,613 | 6/1992 | McGowan | 436/71 |

*Primary Examiner*—Frank Spear
*Assistant Examiner*—Sun Uk Kim
*Attorney, Agent, or Firm*—Michael A. O'Neil

[57] ABSTRACT

An apparatus for separating isoanalytes and measuring analytes in fluids includes a two-chambered filtration device having a filter positioned parallel to the majority flow of fluids. The apparatus uses continuous flow filtration to separate one component from other fluid components.

An alternative apparatus for separating isoanalytes and measuring analytes in fluids includes a reaction chamber which uses intermittent flow filtration with a piston/valve assembly to separate one component from other fluid components.

A method for separating isoanalytes and measuring analytes in fluids comprises the steps of: mixing a fluid sample and a precipitating reagent; directing the mixture to a filtration device; adding a color reagent; directing the filtrate to an analyzer; replacing the fluid sample with a wash solution; and replacing the precipitating reagent with a cleaning solution.

An alternative method for separating isoanalytes and measuring analytes in fluids comprises the steps of: directing a fluid sample to a reaction chamber; directing a precipitating reagent to the reaction chamber; mixing the fluid sample and the precipitating reagent; applying pressure to the reaction chamber; adding a color reagent to the filtrate; directing the filtrate to an analyzer; and replacing the fluid sample and the precipitating reagent with a cleaning solution.

1 Claim, 3 Drawing Sheets

METHOD FOR SEPARATING ISOANALYTES AND MEASURING ANALYTES IN FLUIDS

TECHNICAL FIELD

This invention relates to apparatus and methods for determining selected analyte levels in fluids and, more particularly, to an apparatus and method for determining the HDL cholesterol level in blood serum or plasma.

BACKGROUND OF THE INVENTION

Scientists have discovered that elevated cholesterol levels may be related to various diseases, including coronary heart disease. However, studies have indicated that an individual's high-density lipoprotein (HDL) cholesterol level is inversely proportional to his risk of coronary heart disease.

Responding to the suggested link between cholesterol level and heart disease, many individuals began requesting blood tests to determine baseline levels and changes in their cholesterol levels. Scientists created tests to determine total cholesterol levels, as well as individual concentrations of low-density lipoprotein (LDL), very low-density lipoprotein (VLDL) and HDL cholesterol.

Prior art techniques for measuring HDL cholesterol levels involving selective precipitation, electrophoresis, or ultracentrifugation have several disadvantages. Prior art methods require pretreatment of the blood sample, addition of various reagents at different stages in the test process, and centrifugation or electrophoretic separation, and subsequent color development, or ultracentrifugation and subsequent visualization.

Due to the time required by these additional steps, HDL cholesterol analysis heretofore has not been automated like other blood tests. Therefore, the original blood sample must be separated into more than one aliquot, or more than one sample must be taken from each individual in order to perform any group of test procedures that include HDL cholesterol analysis. As a result, current techniques for determining HDL cholesterol levels are complicated, slow and labor-intensive.

SUMMARY OF THE INVENTION

The present invention comprises a highly practical, fully automated apparatus and method for determining cholesterol levels in blood serum or plasma which overcome the foregoing disadvantages associated with the prior art.

The apparatus includes a two-chambered housing having a filter positioned parallel, rather than perpendicular, to the majority flow of fluids. The apparatus uses continuous flow filtration to separate the HDL cholesterol from other blood components.

An alternative embodiment of the apparatus includes a single-chambered housing having a filter positioned near the bottom of same. The apparatus uses a valve and piston assembly and intermittent flow filtration to separate the HDL cholesterol from other blood components.

A method for determining HDL cholesterol concentration in a blood serum/plasma sample includes the steps of mixing a blood serum/plasma sample with a precipitating reagent; directing the mixture into the first chamber of a filter housing; adding a color reagent to the second chamber of the filter housing; directing the filtrate to an analyzer; replacing the blood serum/plasma sample with a wash sample; replacing the precipitating reagent with a cleaning solution; and repeating the remaining steps.

An alternative method for determining HDL cholesterol concentration in a blood serum/plasma sample includes the steps of directing a blood serum/plasma sample into a filter housing; directing a precipitating reagent into the filter housing; mixing the blood serum/plasma sample with the precipitating reagent; adding a color reagent to the filtrate; directing the filtrate to an analyzer; replacing the blood serum/plasma sample and precipitating reagent with cleaning solution; and repeating the remaining steps.

Because residual precipitate on the filter in the filter housing is dissolved by the cleaning solution after each blood serum/plasma sample, both embodiments of the apparatus may be used to analyze a large number of samples without obstruction of the filter. As a result, a large number of samples may be run in a short time period. Such an automated process permits high-volume, low-cost HDL cholesterol testing.

DESCRIPTION OF THE DRAWINGS

For a more complete understanding of the present invention and the advantages thereof, reference is now made to the following Detailed Description taken in conjunction with the accompanying Drawings in which.

DETAILED DESCRIPTION

Figure 1A:
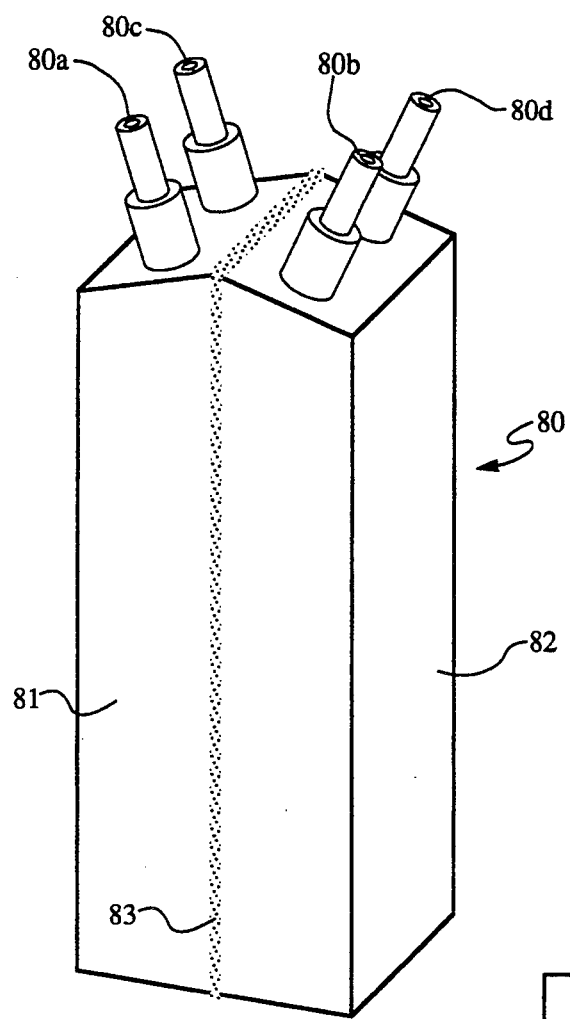
FIG. 1A is an enlarged perspective view of a filtration device according to the present invention.

Referring now to the Drawings, wherein like reference characters designate like or similar parts throughout the three views, FIG. 1A is an enlarged perspective view of a filtration device 80 according to the present invention.

Figure 1B:
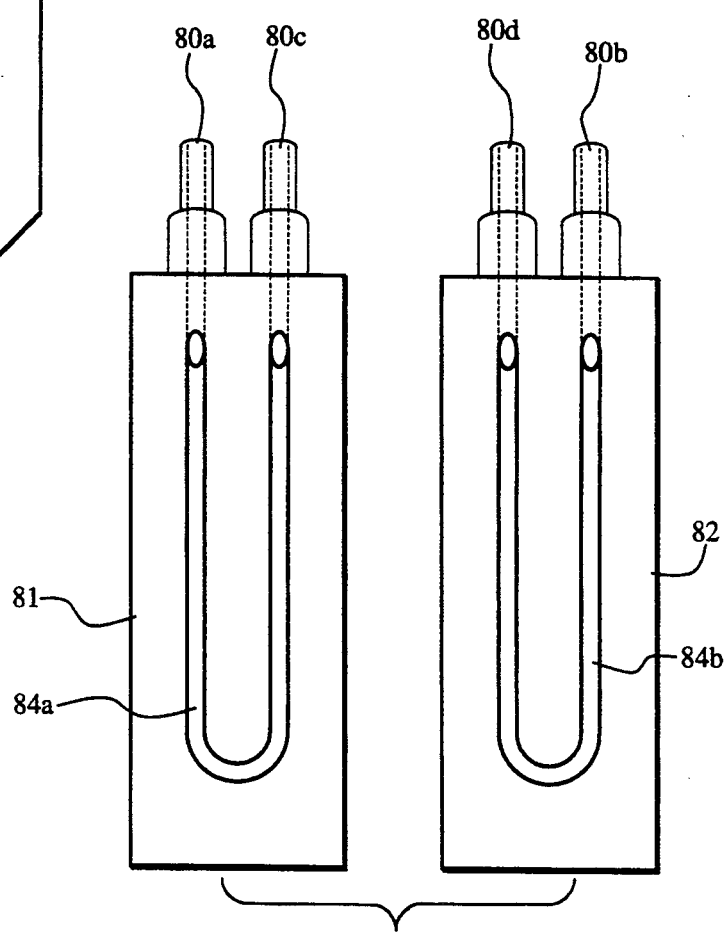
FIG. 1B is an alternative view of the first block and the second block of the filtration device shown in FIG. 1A, showing the opposing faces of each block.

The filtration device 80 shown in FIGS. 1A and 1B is an example of a filtration device that may be used in the apparatus. It will be understood that other types of filtration devices may also be used for the continuous flow filtration process described herein. For example, the fluid flow groove configuration or placement of the intake and output points may be varied as desired.

Blood samples evaluated in the apparatus may be blood serum or plasma. Throughout the remainder of the specification, the term blood serum is used for clarity, it being understood that a blood serum or blood plasma specimen may be used.

Two basic steps have occurred prior to a blood serum sample reaching filtration device 80. Blood serum has been mixed with a precipitating reagent, initiating separation of the LDL and VLDL cholesterol components from the rest of the sample. The result is a slurry of precipitated LDL and VLDL cholesterol and HDL cholesterol in solution. Substantially simultaneously, air bubbles have been injected into the cholesterol slurry. Following this mixing and injection, the cholesterol slurry is directed to filtration device 80.

Filtration device 80 comprises two equal-sized, substantially solid blocks: a first block 81 and a second block 82. Carved into the opposing surfaces of the first block 81 and the second block 82 are fluid flow grooves 84a and 84b, respectively. The groove patterns in blocks 81 and 82 are mirror images of each other. The majority of fluids flow through the two blocks 81 and 82 along fluid flow grooves 84a and 84b. Tubes connect fluid flow grooves 84a and 84b with intake and output points in the two blocks.

Although the fluid flow groove pattern shown in FIGS. 1A and 1B is U-shaped, other groove patterns, such as spiral, oval, or straight may also be used. Any groove pattern that permits sufficient contact between the two fluid streams flowing through blocks 81 and 82 may be used.

A bolt assembly (not shown) holds blocks 81 and 82 together. The pressure applied by the bolt assembly on the two blocks also prevents fluid leakage around the filter 83. Positioning pins (not shown) ensure proper alignment of fluid flow grooves 84a and 84b in blocks 81 and 82.

Sandwiched between fluid flow grooves 84a and 84b of blocks 81 and 82 is a filter 83. Different shaped filters, such as circular or rectangular, may be used, as long as filter 83 completely covers grooves 84a and 84b of the two blocks. Filter 83 may be composed of nylon, cellulosic material, or alumina. In the preferred embodiment, filtration device 80 uses a 0.45 micron nylon filter.

Filter 83 is positioned parallel, rather than perpendicular, to the majority flow of fluids through filtration device 80. However, due to the positive pressure in fluid flow groove 84a relative to fluid flow groove 84b, a small amount of fluid flows across filter 83.

Filtration device 80 has two intake points. One intake point 80a receives the cholesterol slurry from a mixing coil positioned near filtration device 80. The other intake point 80b receives a cholesterol color reagent. The color reagent is added to make the HDL cholesterol easily registrable after it passes across the filter, reacts and is analyzed in the photometer.

When the cholesterol slurry enters filtration device 80, most of the precipitated LDL and VLDL cholesterol fractions move through filtration device 80. A small amount of precipitated LDL and VLDL cholesterol remains in groove 84a against filter 83. Filter 83 traps the precipitate, and prevents it from moving from fluid flow groove 84a into fluid flow groove 84b. The HDL cholesterol in solution, however, moves easily across filter 83 into the moving stream of cholesterol color reagent flowing through fluid flow groove 84b.

The precipitate exits filtration device 80 through output point 80c and moves to a waste storage area. The residual precipitate on filter 83 will be dissolved when sample wash solution is run through filtration device 80 after a blood serum/plasma specimen is analyzed.

Liquids flow into and out of filtration device 80 at a predetermined rate. Positive pressure is maintained in fluid flow groove 84a relative to fluid flow groove 84b due to the rates at which fluids are pumped into and out of the two grooves, respectively. Preferably, relatively constant transfilter pressure is maintained in filtration device 80 to encourage fluid flow from groove 84a into groove 84b.

Filtration device 80 has two output points. From output point 80c, waste, including the LDL and VLDL cholesterol precipitate, moves out of fluid flow groove 84a of block 81 of filtration device 80 via a waste line to a waste receptacle. From the other output point 80d, the filtered and now reacting solution is directed to a heating bath coil and then to an analyzer for an HDL cholesterol reading.

Referring now to FIG. 1B, there is shown an alternative view of block 81 and block 82 of the filtration device illustrated in FIG. 1A, showing the opposing faces of each block. When the apparatus is operating, a filter (not shown) is placed between blocks 81 and 82. Fluid flow grooves 84a and 84b in the first and second blocks, respectively, direct the flow of the two fluid streams through filtration device 80.

Fluids enter blocks 81 and 82 through intake points 80a and 80b, respectively, move along fluid flow grooves 84a and 84b, and exit blocks 81 and 82 via output points 80c and 80d. The HDL cholesterol in solution moves across the filter from fluid flow groove 84a in the first block 81 into fluid flow groove 84b in the second block 82, and mixes with the color reagent.

In the preferred embodiment, fluids move in the same direction along grooves 84a and 84b of the first 81 and second blocks 82, respectively, of filtration device 80. As an alternative, the fluid flow may be changed so that fluids move in opposite directions through grooves 84a and 84b. For example, the incoming line to intake point 80b and the outgoing line from output point 80d of block 82 could be switched, while the lines to intake point 80a and output point 80b of block 81 remained the same.

Figure 2:
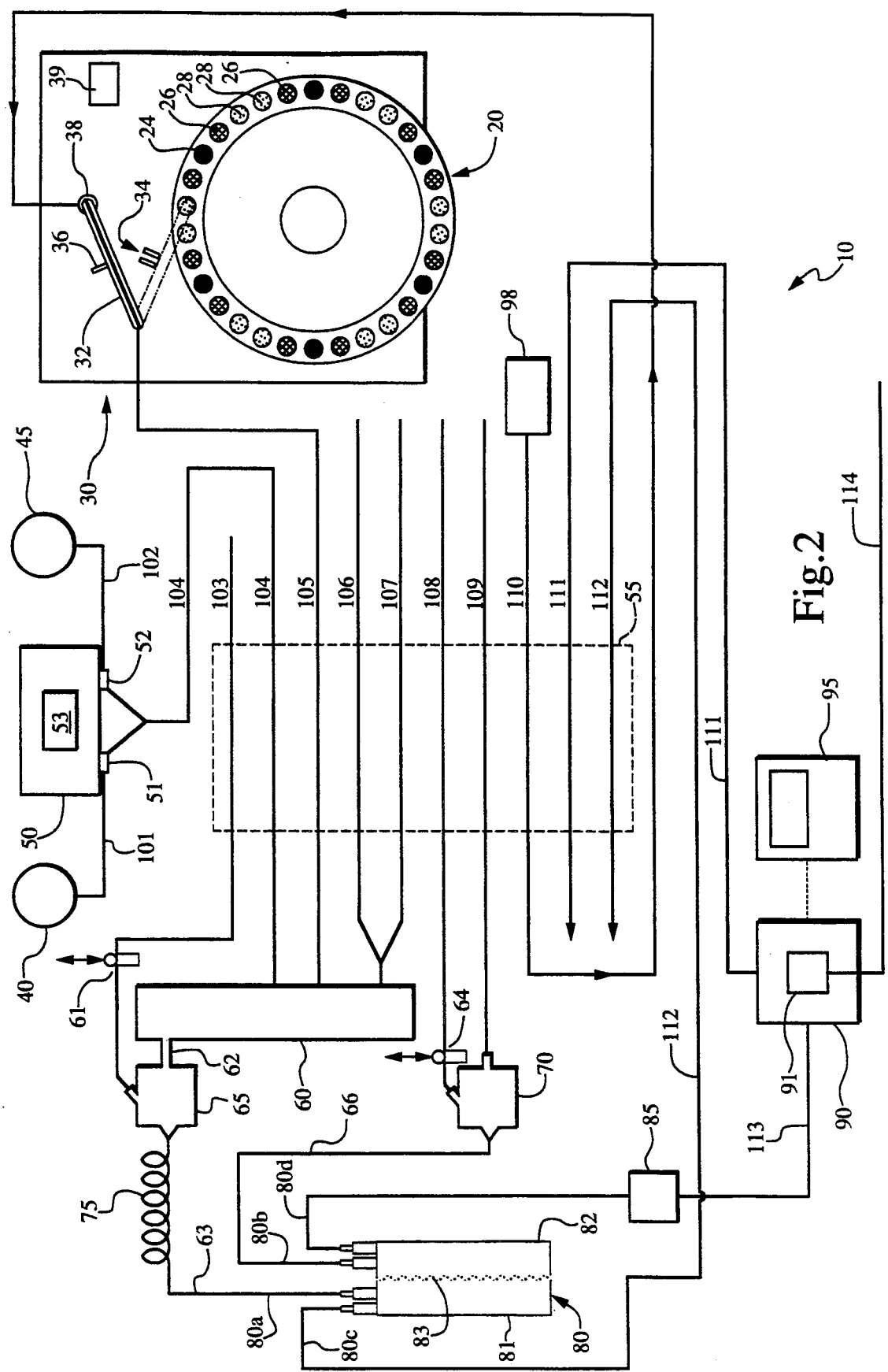
FIG. 2 is a schematic diagram of an apparatus illustrating the features of the invention.

Referring now to FIG. 2, there is shown a schematic drawing of an apparatus 10 for separating isoanalytes and measuring selected analytes in blood serum.

As used herein, an isoanalyte is a second or alternative reactant in an analysis that may chemically resemble the primary analyte, and which reacts, if present, in a way to influence the validity and amount of the final analytical result. Examples of isoanalytes include homologs, isoenzymes, isoforms, isomers, interfering substances, cross reactants, and labeled analytes.

Many of the component parts of the apparatus are well known in the art and do not form part of the present invention. In addition, any of the components or groups of components may be substituted with other similarly functioning components.

A rotary sample wheel 20 holds specimen tubes containing blood samples which will be tested for HDL cholesterol concentrations, and sample wash specimens. Due to space limitations, sample wheel 20 in FIG. 2 has thirty spaces for use in analyzing six blood serum samples. Preferably, a conventional forty-sample wheel which holds eight blood serum specimens is substituted for the thirty-sample wheel shown.

To prevent possible clogging of the filter 83 during the filtration process, every opening in sample wheel 20 does not hold a specimen tube containing blood serum. Instead, each specimen tube holding blood serum 24 is positioned so that it will be followed by specimen tubes containing various sample wash solutions 26 and 28.

Preferably, one blood serum specimen tube 24 is followed by four sample wash tubes. This arrangement ensures that filtration device 80 is flushed out between different blood serum samples, that an accurate HDL cholesterol reading is obtained for each blood serum sample, and that apparatus 10 can test numerous blood serum samples before it needs to be cleaned.

In addition to holding blood serum sample tubes 24, sample wheel 20 holds specimen tubes containing two different sample wash solutions. Some specimen tubes 26 hold a phosphate buffer solution. The phosphate buffer solution may be prepared by dissolving 7.83 g $K_2HPO_4$, 6.12 g $KH_2PO_4$, and 0.75 g NaOH in 1 liter of deionized water. The pH may be adjusted to 7.1±0.1 with 1N NaOH or 1N HCl as necessary.

Other sample wash tubes 28 hold phosphate buffer solution to which 5% NWA, a wetting agent, has been added. The second phosphate buffer solution may be prepared by adding 5 ml of Technicon product T-21-0813-17 to 95 ml of phosphate buffer solution.

In the preferred embodiment, the arrangement of the sample tubes is: blood serum sample 24, phosphate buffer 26, 95% phosphate buffer with 5% NWA (V/V) 28, 95% phosphate buffer with 5% NWA (V/V) 28, and phosphate buffer 26. Thus, every fifth specimen tube holds a blood serum sample.

Positioned in close proximity to sample wheel 20 is a sampler 30. Sampler 30 extracts blood serum and sample wash specimens from sample wheel 20 for delivery to the main injection block 60. The sampler 30 generally comprises a probe 32, sample wash reservoir 38, sensing device 34, timing device 39, and optical barrier or sensor flag 36.

The probe 32 may be connected to a sample line 105. Preferably, the first end of sample line 105 attaches to the hollow probe 32 and the second end of sample line 105 connects through a peristaltic pump 55 to the main injection block 60. Other methods may also be used to deliver the sample to sample line 105.

A sample wash reservoir 38 is positioned near probe 32. Reservoir 38 contains sample wash, such as phosphate buffer solution, that will be used to clean apparatus 10, and particularly filter 83, between blood serum samples. Sample wash is continually pumped from a sample wash source 98 through a line 110 to the sample wash reservoir 38 to ensure that reservoir 38 is always full.

Liquids flow constantly from sampler 30 via pump 55 to the main injection block 60. Probe 32 moves between two positions: extracting a sample from a specimen tube in sample wheel 20, or extracting sample wash from sample wash reservoir 38. Sample wheel 20 indexes or rotates one position every time probe 32 lifts out of a specimen tube.

A sensing device 34, e.g. an infrared sensor, is positioned between sample wheel 20 and sample probe 32. Sensing device 34 is electrically connected to a timer/counter 53 in the switching device 50.

A timing device 39, positioned near sample wheel 20, ensures that all specimens in sample wheel 20 are sampled for the proper time, and indexes wheel 20.

The amount of time probe 32 extracts blood serum or sample wash from each specimen tube, and sample wash from sample wash reservoir 38 may be varied as desired. A 1:2 sampling ratio between specimen tube and sample wash reservoir is desirable. In the preferred embodiment, probe 32 samples each specimen tube for twenty seconds and sample wash reservoir 38 for forty seconds.

Attached to sample probe 32 is an optical barrier or sensor flag 36. Sensor flag 36 "trips" sensing device 34 each time probe 32 moves from the sample wash reservoir position.

Sensor flag 36 interacts with sensing device 34, and thus, with the timer/counter 53 positioned inside switching device 50, to coordinate timely delivery of precipitating reagent and sample wash solution to the main injection block 60. The timer/counter 53 receives all of its instructions from sensing device 34, and is, in effect, a "slave" to sampler 30.

When the counter component of the timer/counter 53 in switching device 50 counts the first, sixth, eleventh, etc. "trip" of sensor flag 36, signifying that a blood serum specimen is being sampled, the timer component of timer/counter 53 initiates flow of precipitating reagent from the precipitant container 40.

Together, timer/counter 53 and sensing device 34 ensure that precipitating reagent, not sample wash solution, flows to the main injection block 60 each time probe 32 samples a blood serum specimen.

Instead of filling sample wheel 20 with blood serum specimens 24 alternating with wash solution samples 26 and 28, the sample wheel may be loaded exclusively with blood serum samples. Using this approach, a second sample wash reservoir (not shown) holding phosphate buffer solution with 5% NWA may be positioned near sample wash reservoir 38 containing phosphate buffer solution.

Using the dual wash solution container approach, probe 32 would sample a blood serum sample tube 24 for a designated time period, and then extract a sample from sample wash reservoir 38. Then probe 32 would sample phosphate buffer solution containing 5% NWA from the second sample wash reservoir. Probe 32 would remain in the second wash solution container for the time period allocated to two specimens. The probe would then return to the first wash solution reservoir 38, remaining in the phosphate buffer solution for one time period. After the two sample wash solutions were sampled for the time allocated to four samples, probe 32 would return to sample wheel 20, select another blood serum specimen, and transport it to the main injection block 60 via line 105.

While it would not increase the blood serum specimen analysis rate, this approach would allow forty, rather than eight blood serum specimens to be loaded at one time.

A container 40 holds a quantity of precipitating reagent and a container 45 holds a quantity of sample wash. A conventional precipitating reagent known in the art is used to separate the LDL and VLDL cholesterol fractions from the HDL cholesterol component. The precipitating reagent may be prepared by diluting Technicon product T01-2801-56 to 45% of its original concentration, e.g. by adding 5.5 ml deionized water to 4.5 ml of product T01-2801-56. The active ingredient in the precipitating reagent is dextran sulfate.

A phosphate buffer solution as sample wash is desirable. The same phosphate buffer solution may be used in sample wash container 45 and in sample wash reservoir 38 associated with sampler 30.

Precipitant container 40 and sample wash container 45 are connected to the main injection block 60 via lines 101 and 102, respectively, which join to form a single line 104. Selection of precipitating reagent or sample wash through lines 101, 102 and 104 is controlled by switching device 50 having on-off valves, e.g. solenoid pinch valves. Preferably, two solenoid pinch valves 51 and 52 are used to control the flow of precipitant and sample wash from holding containers 40 and 45, respectively.

When the solenoid pinch valves 51 and 52 connected to switching device 50 are in the open-closed position, line 101 to precipitating reagent container 40 is open, and line 102 to sample wash container 45 is closed. Alternatively, when the pinch valves are in the closed-open position, line 101 to precipitant container 40 is closed and line 102 to sample wash container 45 is open. Because both lines 101 and 102 are never open or closed at the same time, liquids are constantly moving towards filtration device 80 from one of the two holding containers 40 or 45 at any given time.

Switching device 50 controls the flow of precipitating reagent and sample wash solution to the main injection block 60 as a function of time. A timer/counter 53 positioned inside switching device 50 is connected electrically to sampler 30. The timer/counter 53 coordinates with sensing device 34 of sampler 30 to regulate the flow of precipitant and sample wash solution to the main injection block 60. Preferably, there is a five minute cycle: precipitating reagent flows for eighty seconds and sample wash flows for two hundred twenty seconds.

It is important that the precipitating reagent and blood serum specimen reach the main injection block 60 at the same time so that the necessary chemical reactions occur to separate the LDL, VLDL, and HDL cholesterol components. The timer/counter 53 may be adjusted as necessary to ensure that precipitating reagent arrives at the main injection block 60 at the appropriate time.

A series of flexible lines or tubes add or remove fluids during the cholesterol analysis process. Each tube may have a different cross-section, depending on the component flowing through it. Different-sized tubes ensure that the correct quantity of each component is delivered to the appropriate area of the apparatus.

Each tube is placed on a pump 55. Pump 55 causes the components in the tubes to move peristaltically through the tubes. The pump creates positive pressure at the tube exits and negative pressure at the tube entrances to initiate movement of the components within the tubes.

In the preferred embodiment, a conventional pumping apparatus comprising a series of rollers (not shown) sweeps across the flexible tubes, pressing them against a fixed platen or plate (not shown) and causing peristaltic movement of the components through the tubes.

Line 101 from precipitating reagent container 40 and line 102 from sample wash container 45 join to form single line 104 which delivers precipitating reagent or sample wash to the main injection block 60, depending on the positions of solenoid pinch valves 51 and 52.

Air line 103 connects an air source (room air) to a second injection block 65. Air bubbles are intermittently added to the second injection block 65 to effectuate mixing of the components in block 65 and scrubbing of the interior of apparatus 10. The air bubbles will be removed at a later stage by a debubbler 91.

Until air is needed, a release bar 61 rests against air line 103, keeping the line closed. In the preferred embodiment, a release bar 61 is used to control the movement of air out of line 103. Bar 61 is mechanically controlled, not pressure controlled. The bar lifts periodically, and air in line 103 is delivered to injection block 65. Bar 61 then returns to its original closed position. The rate at which air is injected into injection block 65 may be varied as desired.

Line 105 delivers a blood serum sample or sample wash specimen from sampler 30 to the main injection block 60. Lines 106 and 107 transport saline to the main injection block 60. Saline solution is used to dilute the blood serum/precipitating reagent mixture to the appropriate strength to achieve the desired chemical reactions. The 0.9% saline solution may be prepared by dissolving 9 g of sodium chloride in 1 liter of deionized water.

A second air line 108 adds air bubbles into a third injection block 70. As with the first air line 103, this air line 108 has a release bar 64 which allows air to move into the third injection block 70 at predetermined intervals. A single release bar may be used to control the flow of air from air lines 103 and 108 into injection blocks 65 and 70 as desired. The air bubbles have a mixing effect on the solution and a scrubbing effect on the interior of apparatus 10.

Also connected to the third injection block 70 is a line 109 which adds a cholesterol color reagent. The color reagent may be of the cholesterol esterase/oxidase type that is readily available and well known in the art, such as AMRESCO product #1237.

When a cholesterol color reagent is added to the filtered HDL cholesterol solution, a chemical reaction occurs over time, ultimately producing color proportional in intensity to the HDL cholesterol concentration in the solution. By the time the filtered solution reaches the colorimeter 90, substantially all of the HDL cholesterol in the solution has oxidized, with a resultant proportional production of a colored dye.

The change in absorbance at a certain wavelength caused by the reaction of the color reagent and the solution is detectable by instrumentation and sometimes visible to the human eye.

When mixed with the filtered solution, the cholesterol color reagent will produce color in response to any cholesterol in the solution. Because the apparatus has previously removed the LDL and VLDL cholesterol fractions, the only cholesterol remaining in the solution that can react with the color reagent and produce color is the HDL cholesterol. Therefore, when the colored solution is analyzed in colorimeter 90, the reading will be of the HDL cholesterol concentration.

A line 110 receives sample wash, such as phosphate buffer solution, from a sample wash source 98, and delivers it to sample wash reservoir 38. Line 110 ensures that sufficient quantities of sample wash are always present in sample wash reservoir 38.

The remaining lines are waste lines. A line 111 removes waste liquids from the colorimeter 90 after the filtered, colored solution has been tested. Line 112 transports waste, including precipitated LDL and VLDL cholesterol, from block 81 of filtration device 80. Waste line 114 carries air bubbles removed from the filtered solution by debubbler 91.

Apparatus 10 includes three injection blocks: the main injection block 60, a second injection block 65, and a third injection block 70. Preferably, the main injection block 60 and the second injection block 65 are connected to each other. The main injection block 60 receives the blood serum sample or sample wash specimen, precipitating reagent or sample wash solution, and saline solution. In the main injection block, chemical reactions occur which produce a slurry of precipitated LDL and VLDL cholesterol and HDL cholesterol in solution.

The cholesterol slurry passes from the first injection block 60 into the second injection block 65 through passageway 62. In the second injection block 65, air bubbles are added through air line 103. The air bubbles serve two main functions: they help mix the components and they have a scrubbing effect on the interior of apparatus 10. The air bubbles will be removed at a later stage in the analysis process by debubbler 91.

The third injection block 70 receives cholesterol color reagent and air bubbles. The color reagent solution flows into filtration device 80 through line 66. The chemical reaction between the filtered HDL cholesterol solution and the cholesterol color reagent produces color in the previously colorless solution, so that the HDL cholesterol level can be determined by colorimeter 90.

Connected to the second injection block 65 is a mixing coil 75. Mixing coil 75 ensures that all of the components are thoroughly mixed for the proper time. The mixing coil also provides essential timing for the chemical reactions. After the mixing, the cholesterol slurry moves through line 63 into the fluid flow groove of block 81 of filtration device 80.

As described above, a portion of the HDL cholesterol solution passes through filter 83. Precipitated LDL and VLDL cholesterol are retained in the fluid flow groove of block 81, as well as on the filter surface exposed to the fluid flow groove. After filtration, the HDL cholesterol solution begins to mix with the cholesterol color reagent in the fluid flow groove of block 82. The reacting solution moves from the fluid flow groove of block 82 of the filtration device to a heating bath coil 85 where the solution is allowed to incubate at room temperature.

Incubating the solution allows greater color development, which improves the sensitivity of the colorimeter 90 in determining the HDL cholesterol level. Preferably, the solution incubates for approximately ten minutes to allow an optimal color reaction.

Following incubation in heating bath coil 85, the reacting, colored solution moves via line 113 into colorimeter 90. The air bubbles which were added at an earlier phase are removed by debubbler 91 located inside colorimeter 90. If left in the solution, the air bubbles would cause an optical disturbance resulting in an artificial absorbance peak when the solution is read by colorimeter 90.

Waste line 114 transports the removed air bubbles from debubbler 91 to a waste storage area. Alternatively, the air bubbles may be suppressed electronically, obviating the need for a debubbler.

A photometer/colorimeter 90 well known in the art may be used to determine the HDL cholesterol concentration in the blood serum sample. The reacted solution produces a characteristic absorbance peak which can be compared to a known standard to determine the HDL cholesterol level in the blood serum sample. Photometer 90 is attached to a recording device 95 which produces a permanent record of the HDL cholesterol reading of the blood serum sample. This information may also be transmitted directly from photometer 90 to any of a variety of data storage, data reduction, or data transmission devices.

Upon completion of the HDL cholesterol analysis of the blood serum sample, the process recommences using a sample wash specimen. If a second blood serum sample were used immediately, filter 83 in filtration device 80 would eventually clog, requiring that apparatus 10 be shut down and cleaned.

A sample wash specimen is delivered to the main injection block 60 via sample line 105, and solenoid pinch valves 51 and 52 reposition to the closed-open position. Phosphate buffer solution flows from sample wash container 45 into lines 102 and 104. The remaining process follows as if a blood serum sample were being analyzed.

The phosphate buffer solution, in the absence of precipitating reagent, dissolves residual precipitate on filter 83 in filtration device 80. The cycle using sample wash solution cleans filter 83 of precipitated cholesterol without scrubbing or otherwise damaging filter 83, and without necessitating shutting down the apparatus. When the sample wash specimen is analyzed by photometer 90, it produces an absorbance peak similar to that produced by the HDL cholesterol in the blood serum sample.

Following the first cycle using the sample wash specimen, a second wash specimen containing 5% NWA is run through the apparatus. The second wash specimen produces an even smaller peak than the first wash specimen. Both wash peaks may be suppressed electrically, if desired.

Two additional sample wash specimens, one with and another without 5% NWA, are run through the apparatus. Due to the dissolution of residual precipitate on filter 83 by the previous wash specimens, the final two wash specimens produce little to no absorbance peaks when screened by photometer 90.

After four wash specimens have been run through the apparatus, sampler 30 selects another blood serum sample from sample wheel 20, and the process begins again.

The pattern, frequency, and composition of wash specimens and precipitants may be varied as needed to optimize the analytical process.

Although the present invention has been described as an apparatus and method for measuring HDL cholesterol levels, it may also be used to analyze levels of other blood serum components. For example, the apparatus and method may be used to measure levels of isoanalytes of acid phosphatase (ACP), alkaline phosphatase (ALKP), creatine kinase (CK), variants of hemoglobin (Hb), and lactate dehydrogenase (LDH).

In addition, although the apparatus and method have been described for use with blood serum or plasma, the apparatus and method may also be used for other fluids, e.g. spinal fluid, urine, etc. Moreover, if a radioactivity counter(s) is added to the apparatus, any substance measurable by a radio-immunoassay procedure (RIA) may be measured by continuous flow filtration using the present invention.

Essentially the only limitation on the use of the apparatus and method to determine levels of isoanalytes or fluid components is the type of precipitants, labeled antibodies and antigens, antigens, wash solutions and mechanical filters which are available. If the fluid component can be measured colorimetrically or via RIA, the present invention may be used to provide high-volume, low-cost analysis after it separates the isoanalytes.

OPERATION OF PREFERRED EMBODIMENT

The photometer, recorder, switching device and pump are turned on. The switching device pinch valves are placed in the open-closed position so that the line to the precipitating reagent is open and the line to the sample wash solution is closed.

Blood serum and sample wash specimens are arranged in a sample wheel, with four sample wash tubes after each blood serum sample tube. A blood serum specimen tube is aligned with the sampler probe.

The sampler probe extracts a constant portion of blood serum using the action of the peristaltic pump. Precipitating reagent, saline solution and a blood serum sample flow through their respective lines to the main injection block. The LDL and VLDL cholesterol components precipitate, leaving the HDL cholesterol component in solution.

The cholesterol slurry flows from the main injection block into the second injection block. Air bubbles are added, and the slurry moves to the mixing coil, where it is thoroughly mixed. A cholesterol color reagent and air bubbles flow into the third injection block, are mixed together and then delivered to the second block of the filtration device.

The slurry moves into the fluid flow groove of the first block of the filtration device, where a portion of the HDL cholesterol in solution passes across the filter. Residual precipitate from the precipitation process remains trapped on the filter. A pump is constantly driving liquids through the filtration device, creating a constant pressure differential across the filter positioned between the two blocks.

The filtered solution reacts with the cholesterol color reagent in the fluid flow groove of the second block of the filtration device, with a resultant proportional production of colored dye. The reacting solution moves to a heating bath coil to allow greater color development. Waste moves out of the filtration device to a waste receptacle.

The colored solution flows into a photometer where air bubbles are removed and the HDL cholesterol level in the solution is determined. The dye in the solution produces a characteristic light absorption which is monitored to form an electric peak. The dye's intensity, representing the HDL cholesterol concentration in the sample, is recorded on a recording device attached to the photometer. The solution is removed from the photometer, and waste liquids move out of the photometer to a waste receptacle.

After a predetermined time, the pinch valves in the switching device reposition to the closed-open position. The sampler extracts a sample wash specimen from the sample wheel. Sample wash, saline solution and phosphate buffer solution flow into the main injection block. No precipitation occurs.

The solution flows into the second injection block where air bubbles are added. The solution moves into the mixing coil where the components are thoroughly mixed.

Cholesterol color reagent and air bubbles flow into the third injection block, where they are mixed and then delivered to the fluid flow groove of the second block of the filtration device. The sample wash/phosphate buffer mixture enters the fluid flow groove of the first block of the filtration device.

The phosphate buffer solution dissolves residual precipitate trapped on and in the filter from the previous blood serum sample. Waste exits the filtration device and moves to a waste container, although some redissolved precipitate moves across the filter and mixes with the color reagent.

The solution flows out of the fluid flow groove of the second block of the filtration device to a heating bath coil, where it incubates at room temperature. The solution moves to the photometer, where air bubbles are removed by a debubbler. A color reading representing the HDL cholesterol level of the solution is taken. Due to the redissolved precipitate that crossed the filter, the colored wash sample solution produces an absorbance peak similar to that produced by the previous blood serum specimen.

The cholesterol reading of the sample wash solution is recorded on the recording device attached to the photometer. The solution is removed from the photometer, and waste liquids move to a waste container.

The sampler selects another sample wash specimen, and the process begins again. When analyzed in the photometer, the second sample wash specimen produces a smaller absorbance peak than either the blood serum sample or the first sample wash specimen.

The sampler selects third and fourth sample wash specimens to be run through the apparatus. The third and fourth sample wash specimens produce little to no absorbance peaks when analyzed by the photometer. After the fourth sample wash specimen is removed from the photometer, the sampler selects a blood serum sample and the process begins again.

Figure 3:
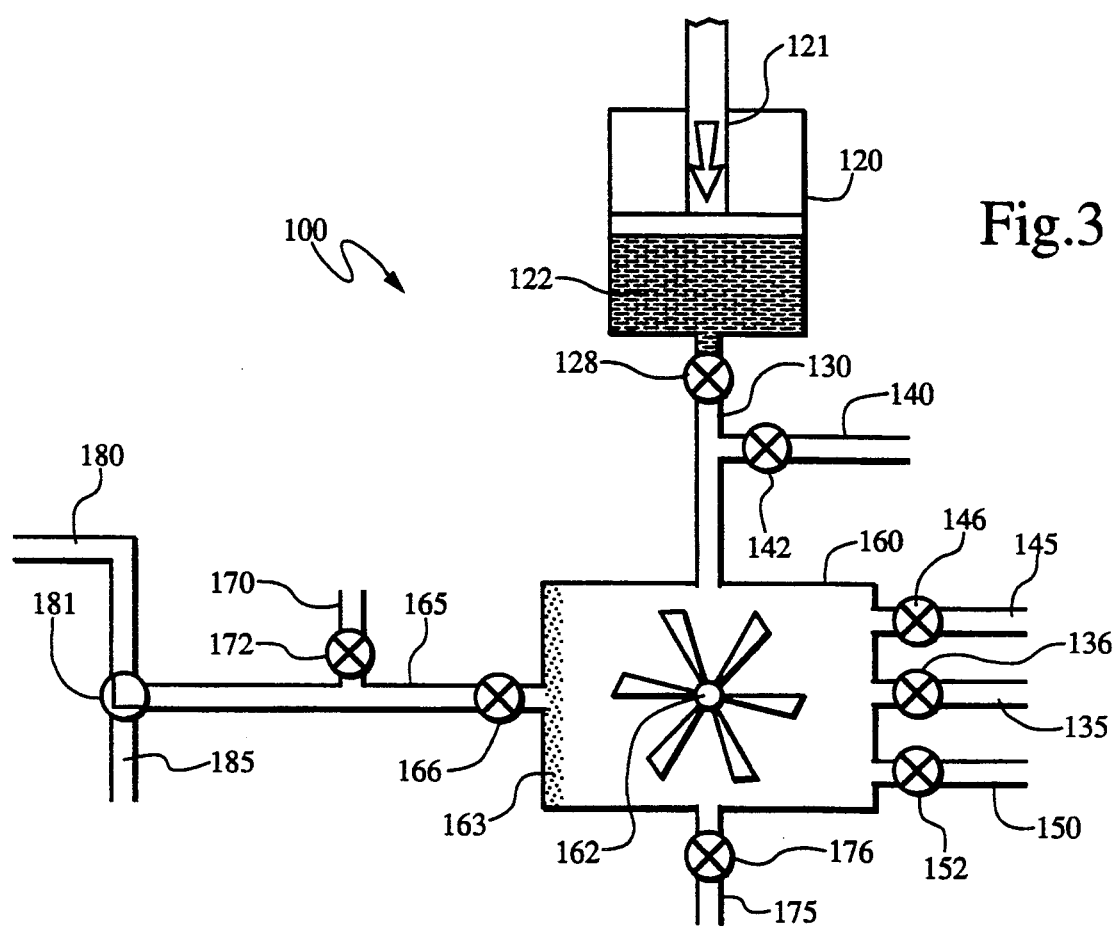
FIG. 3 is a schematic diagram of an alternative embodiment of the invention.

Referring now to FIG. 3, there is shown a schematic diagram of an alternative embodiment of an apparatus for separating isoanalytes and measuring selected analytes in blood serum. The apparatus 100 uses the chemical components previously described in reference to the preferred embodiment of the invention.

Unlike the preferred embodiment, the alternative embodiment does not use peristaltic movement to propel and pull liquids into and out of a reaction chamber. Instead, apparatus 100 uses a piston and valve assembly. Whereas the preferred embodiment uses continuous flow filtration to filter the HDL cholesterol component from other blood serum components, the alternative embodiment uses intermittent flow filtration to accomplish same.

A housing 120 includes a pressure device 121, such as a piston, plunger or syringe, and a pressure chamber 122. The apparatus 100 may work pneumatically or hydraulically using plunger 121 and pressure chamber 122 to force HDL cholesterol in solution through a filter 163 positioned within a reaction chamber 160. The plunger 121 moves other components into and out of reaction chamber 160 using the same method.

The amount of pressure exerted on reaction chamber 160 may be varied by adjusting the extent to which plunger 121 is raised or lowered in pressure chamber 122. Preferably, plunger 121 may be raised and lowered to at least four positions, however, other increments are also possible. Any method that moves plunger 121 in predetermined increments will vary the pressure exerted by plunger 121 on reaction chamber 160 if valve 128 is open.

A line 130 connects pressure chamber 122 to reaction chamber 160. When valve 128 is open, plunger 121 may exert pressure on the interior of reaction chamber 160 through line 130.

Intersecting line 130 is line 140 which delivers air from an air source (room air) to reaction chamber 160. A valve 142 attached to line 140 permits the flow of air into and out of pressure chamber 122.

Before and after a blood serum specimen is run through apparatus 100, air is forced through reaction chamber 160 using syringe or plunger 121 in pressure chamber 122. Pressure applied via plunger 121 helps prepare reaction chamber 160 for the next blood serum specimen by removing residual liquids from the chamber.

Attached to lines 130 and 140 are valves 128 and 142, respectively, which regulate movement through the two lines. Preferably, a number of solenoids (not shown) control the operation of the valves, however, other devices known in the art may also be used to open and close the valves.

The apparatus may use separate valves for lines 130 and 140. In the alternative, a single two-position, three-way valve may be used to control delivery of components through lines 130 and 140 to reaction chamber 160.

Connected to line 130 is reaction chamber 160. Reaction chamber 160 contains a mixing/stirring device 162 and a filter 163. The stirring device 162 thoroughly mixes the contents of the reaction chamber 160. Stirring device 162 may be mechanical, magnetic, or some other means known in the art for mixing. The stirring device should gently mix the contents in reaction chamber 160. If the stirring device vigorously mixes the contents of reaction chamber 160 so that the blood serum sample becomes frothy, subsequent analysis of the sample in the colorimeter will be impaired.

Also positioned inside reaction chamber 160 is a filter 163. It is desirable to place filter 163 at the bottom of reaction chamber 160. The filter may be composed of nylon, cellulosic material or alumina.

At certain intervals, pressure is exerted on the interior of reaction chamber 160, via syringe 121 in pressure chamber 122, forcing a portion of the HDL cholesterol in solution through filter 163. Filter 163 traps a portion of the precipitated LDL and VLDL cholesterol components, preventing the precipitate's exit from reaction chamber 160 through effluent line 165.

There are three additional intake lines to reaction chamber 160: the blood serum line 145, the cleaner line 135, and the saline/precipitant line 150. Line 145 carries blood serum samples to reaction chamber 160. A solenoid-operated valve 146 controls the flow of blood serum specimens through line 145.

Line 135 receives sample wash solution, such as phosphate buffer solution, from a wash source (not shown), and transports the cleaning solution to reaction chamber 160. Connected to cleaner line 135 is a valve 136 which is used to regulate the flow of cleaning solution into the reaction chamber.

Wash solution is directed to reaction chamber 160 between blood serum specimens to dissolve residual precipitate on filter 163. If reaction chamber 160 was not cleaned between blood serum specimens, filter 163 would eventually clog.

Line 150 transports a mixture of saline solution and precipitating reagent to reaction chamber 160. Preferably, saline solution and precipitant are mixed together and delivered substantially simultaneously to reaction chamber 160 through line 150. In the alternative, separate lines may be used for saline solution and precipitant delivery. As with blood serum sample line 145 and cleaner line 135, saline/precipitant line 150 has a valve 152 which regulates the flow of the saline/precipitating reagent mixture to reaction chamber 160.

Saline solution is added to the blood serum sample and precipitating reagent to ensure that the mixture is at the proper concentration to achieve the necessary chemical reactions. Precipitating reagent reacts with the blood serum sample to separate the LDL and VLDL components from the HDL cholesterol component.

Preferably, separate lines carry the blood serum specimen and saline/precipitant to reaction chamber 160, however, other configurations are also possible.

There are two output lines that transport fluids from reaction chamber 160. Line 165 carries the filtered and subsequently colored solution to a colorimeter (not shown) for determination of the HDL cholesterol concentration. Valve 166 controls the flow of the filtered solution through line 165.

Connected to effluent line 165 is a line 170 carrying a cholesterol color reagent. Color reagent line 170 adds a cholesterol color reagent to the filtered HDL cholesterol solution so that the HDL cholesterol will be readily detected in the colorimeter. A valve 172 regulates the flow of cholesterol color reagent through line 170.

After the cholesterol color reagent is added through line 170, the color reagent and the filtered HDL cholesterol solution start to react, producing color proportional to the amount of HDL cholesterol in the sample. As the reacting solution moves towards the colorimeter, the concentration of HDL cholesterol decreases, the HDL cholesterol having been oxidized to produce a colored dye in the solution.

The colored solution is directed to a colorimeter for determination of the HDL cholesterol level. As previously described, the HDL cholesterol produces a characteristic absorbance peak when read by the colorimeter.

Line 165 intersects lines 180 and 185. Line 180 carries waste material received from reaction chamber 160. Line 185 carries the filtered, colored solution to the colorimeter.

Intersecting lines 165, 180 and 185 is a two-way, three-position valve 181. Alternatively, a series of pinch valves may be used to control the movement of fluids through lines 180 and 185. In the first position, valve 181 is open, allowing waste to flow through line 180 to a waste storage area. In FIG. 3, valve 181 is in the first position.

In the second position, valve 181 is open, allowing the filtered, colored solution to flow to the colorimeter through lines 165 and 185. In the third position, valve 181 is closed, permitting no fluid movement therethrough.

Line 175 removes waste, including precipitated LDL and VLDL cholesterol, from reaction chamber 160. A solenoid-operated valve 176 controls the flow of waste out of reaction chamber 160 through line 175.

Using the above-described apparatus 100 to separate isoanalytes and measure selected analytes in blood serum is simple. In the initial resting position, all valves of apparatus 100 are closed, and valve 181 is in the third (closed) position. Plunger 121 is in a fully lowered position. Reaction chamber 160 is already filled with precipitating reagent/saline solution.

Valve 142 to air line 140 and valve 128 to pressure chamber 122 open. Plunger 121 moves to a fully raised position. Air fills pressure chamber 122 of housing 120.

Valve 142 to air line 140 closes, and valve 176 to waste line 175 opens. Plunger 121 moves to a fully lowered position. Air and residual liquids are forced out of reaction chamber 160 through waste line 175.

Valve 176 to waste line 175 closes, and valve 142 to air line 140 opens. Plunger 121 moves to a fully raised position, drawing air into pressure chamber 122.

Valve 142 to air line 140 closes, valve 166 to effluent line 165 opens, and valve 181 moves to the first (open) position. Plunger 121 moves to a fully lowered position. Any residual liquid on filter 163 is forced out of reaction chamber 160 through lines 165 and 180 to the waste storage area.

Valve 181 moves to the third (closed) position, and valve 172 to color reagent line 170 opens. Plunger 121 raises to less than a fully raised position, pulling color reagent into line 165. Preferably, plunger 121 moves to one-fourth of the fully raised position. Raising plunger 121 to less than the fully raised position causes color reagent to move into line 165, but not into reaction chamber 160.

Valve 166 to effluent line 165 and valve 172 to color reagent line 170 close, and valve 152 to saline/precipitant line 150 opens. Plunger 121 raises to one-half of the fully raised position. The plunger's action pulls a mixture of saline solution and precipitating reagent into reaction chamber 160.

Valve 152 to saline/precipitant line 150 closes, and valve 146 to blood serum sample line 145 opens. Plunger 121 raises to three-fourths of the fully raised position, pulling a blood serum sample into reaction chamber 160. Valve 146 to sample line 145 closes.

Mixing device 162 in reaction chamber 160 activates. Precipitant and saline solution gently mix with the blood serum sample. Precipitation ensues, producing a slurry of precipitated LDL and VLDL cholesterol and HDL cholesterol in solution.

Mixing device 162 shuts off, and valve 142 to air line 140 opens. Plunger 121 raises to the fully raised position.

Valve 142 to air line 140 closes and valve 166 to effluent line 165 opens. Valve 181 moves to the second (open) position. Plunger 121 moves to the fully lowered position, forcing a portion of the HDL cholesterol in solution through filter 163 in reaction chamber 160.

The filtered HDL cholesterol solution exits reaction chamber 160 through line 165. The colorless HDL cholesterol solution reacts with the color reagent previously injected into line 165, producing a colored solution.

The filtered, colored solution flows through lines 165 and 185 to an incubator (not shown) and then to a colorimeter for measurement of the HDL cholesterol level. The HDL cholesterol level is recorded on a recording device (not shown) attached to the colorimeter. A portion of the precipitated LDL and VLDL cholesterol fractions remains trapped on filter 163 in reaction chamber 160.

Valve 166 to effluent line 165 closes. Excess pressure in reaction chamber 160, if any, may be released by a momentary opening and closing of valve 176. Valve 136 to cleaner line 135 opens, and valve 181 moves to the third (closed) position. Plunger 121 raises to the fully raised position, drawing cleaning solution into reaction chamber 160 through line 135. Wash solution dissolves any residual precipitate remaining on filter 163 in reaction chamber 160.

Valve 136 to cleaner line 135 closes, valve 166 to effluent line 165 opens, and valve 181 moves to the second (open) position. Plunger 121 moves to the fully lowered position. Cleaning solution exits reaction chamber 160 through filter 163 and line 165 and moves to the colorimeter via line 185. This step ensures that the colorimeter is thoroughly clean in preparation for the next blood serum sample.

Valve 136 to cleaner line 135 opens, valve 166 to effluent line 165 closes, and valve 181 moves to the third (closed) position. Plunger 121 raises to the fully raised position and draws a second cleaning solution sample into reaction chamber 160.

Valve 136 to cleaner line 135 closes, valve 166 to effluent line 165 opens, and valve 181 moves to the first (open) position. Plunger 121 moves to the fully lowered position, forcing cleaning solution from chamber 160 via line 165 into line 180. The solution flows to a waste storage area. Running the cleaning solution through effluent line 165 ensures that filter 163 in reaction chamber 160 is clean before the next blood serum sample is run.

Valve 136 to cleaner line 135 opens, valve 166 to effluent line 165 closes, and valve 181 moves to the third (closed) position. Plunger 121 raises to the fully raised position and draws a third sample of cleaning solution into reaction chamber 160.

Valve 136 to cleaner line 135 closes and valve 176 to waste line 175 opens. Plunger 121 moves to the fully lowered position, forcing cleaning solution from chamber 160 via line 175. Waste liquids move to a waste storage area.

Valve 176 to waste line 175 closes and valve 142 to air line 140 opens. Plunger 121 raises to the fully raised position. Pressure chamber 122 fills with air.

Valve 142 to air line 140 closes and valve 176 to waste line 175 opens. Plunger 121 moves to the fully lowered position, forcing air to exit reaction chamber 160 through line 175.

Valve 176 to waste line 175 closes and valve 152 to saline/precipitating reagent line 150 opens. Plunger 121 raises to the fully raised position, pulling a mixture of saline solution and precipitating reagent into reaction chamber 160 through line 150.

Valve 152 to saline/precipitant line 150 closes and valve 142 to air line 140 opens. Plunger 121 moves to the fully lowered position, exhausting air through air line 140.

Valve 142 to air line 140 and valve 128 to pressure chamber 122 close. Apparatus 100 is ready for another blood serum specimen, and the process begins again.

The cleaning steps may be repeated as many times as necessary between blood serum samples to ensure that all liquids have been removed from filter 163, the interior of reaction chamber 160, and from the colorimeter. In addition, the order of the cleaning steps may be varied as desired. Stirring device 162 may be activated during the cleaning steps as necessary.

Although preferred and alternative embodiments of the invention have been illustrated in the accompanying Drawings and described in the foregoing Detailed Description, it will be understood that the invention is not limited to the embodiments disclosed, but is capable of numerous rearrangements, modifications and substitutions of parts and elements without departing from the spirit of the invention.

I claim:

1. Method for filtering components in a fluid sample, comprising the steps of:
   directing a mixture comprising a sample and a precipitating reagent through a first chamber of a housing having first and second chambers and a filter therein;
   substantially simultaneously directing a color reagent through the second chamber of the housing;
   directing a sample across the filter into the second chamber;
   mixing the filtered sample with the color reagent; and
   subsequently directing a wash solution through the first chamber of the housing to remove residual sample therefrom.

* * * * *